United States Patent [19]
Beretich, Sr. et al.

[11] Patent Number: 5,888,518
[45] Date of Patent: Mar. 30, 1999

[54] METHOD FOR PREVENTING AND TREATING COCCIDIOSIS

[76] Inventors: Guy R. Beretich, Sr.; Louis D. Beretich, both of Rte. 3, Box 14, Clinton, N.C. 28328

[21] Appl. No.: 540,595

[22] Filed: Oct. 6, 1995

[51] Int. Cl.$^6$ ..................... A61K 39/012; A61K 31/785; A01N 33/02
[52] U.S. Cl. ...................... 424/271.1; 424/265.1; 424/267.1; 424/269.1; 424/222.1; 424/229.1; 424/93.1; 424/78.16; 424/78.38; 424/184.1; 424/816; 424/826; 530/350; 530/822; 514/2; 514/561; 514/567; 514/649; 514/773; 562/562
[58] Field of Search .............................. 424/265.1, 267.1, 424/269.1, 222.1, 229.1, 93.1, 78.16, 78.38, 184.1, 271.1, 816, 826; 530/350, 822; 514/2, 649, 773, 561, 567; 562/562

[56] References Cited

U.S. PATENT DOCUMENTS

| | | |
|---|---|---|
| 3,692,904 | 9/1972 | Tsutsumi . |
| 4,600,582 | 7/1986 | Stevens et al. . |
| 4,639,372 | 1/1987 | Murray et al. . |
| 4,724,145 | 2/1988 | Murray et al. . |
| 4,761,282 | 8/1988 | Apontoweil et al. . |

OTHER PUBLICATIONS

Zhirnov et al., "Protective Effect of Protease Inhibitors in Influenza Virus Infected Animals," *Archives of Virology* 73, pp. 263–272 (1982).

Lozitsky et al., "Resistance of Mice to Reinfection After E–Aminocaproic Acid Treatment of Primary Influenza Virus Infection," *Acta virol.* 32, pp. 117–122, (1988).

Lozitsky et al, "Effectiveness of the Combined Use of an Inactivated Vaccine and a Proteolysis Inhibitor in the Prevention Of Experimental Influenza," *Zh Mikrobiol Epidermiol Immunobiol* (USSR) Dec. 1985 (12) pp. 49–53.

Chalyi et al., "Protease Inhibitors as Immunomodulators in Experimental Acute Pancreatitis and Staphylococcal Infection," *ZH Mikrobiol Epidemiol Immunobiol* (Russia), Jan.–Feb. 1993, pp. 62–65.

Hart et al., "Effect of Protease Inhibitors On Mitogen Stimulation of Hamster Lymphoid Cells," *Experimental Cell Research* 102 (1976), pp. 253–263.

Yee et al., "Plasminogen–Dependent Activation of Latent Transforming Growth Factor Beta (TGFβ) by Growing Cultures of Osteoblast–Like Cells," *Journal of Cellular Physiology* 157:528–534 (1993).

Puzis et al., "Action of ε–Aminocaproic Acid on the Proteolysis System During Experimental Influenza in Mice," *Acta virol.* 32, pp. 515–521, (1988).

Kagen et al., Dev. Biol. 1973. vol. 31, No. 2, 295–300, abstract only.

*Primary Examiner*—Anthony C. Caputa
*Assistant Examiner*—Khalid Masood
*Attorney, Agent, or Firm*—Rhodes, Coats & Bennett, LLP

[57] ABSTRACT

A method for preventing and treating parasitic infections in animals by administering a lysine analog, such as EACA, to the animals on a continuous basis. In the preferred embodiment, the method of the present invention is directed to preventing and treating coccidial infections in poultry by adding EACA to the daily diet of a poultry flock. EACA may also be administered in ovo before hatching. The administration of EACA enhances the natural immune response of the poultry to the invading coccidial organisms and enables the poultry to combat the parasites without the need for antibiotics. Another aspect of the present invention involves preventing parasitic diseases in humans and animals by prophylactically administering a serine protease inhibitor, such as EACA, as an adjuvant in conjunction with a conventional vaccine effective against the target parasite.

2 Claims, No Drawings

METHOD FOR PREVENTING AND TREATING COCCIDIOSIS

FIELD OF THE INVENTION

The present invention generally relates to the administration of serine protease inhibitors to enhance the immune response of animals to parasitic diseases and, in particular, pertains to the dietary administration of lysine analogs to poultry and livestock to enhance their immune response to protozoal pathogens and thereby prevent and treat coccidiosis.

BACKGROUND OF THE INVENTION

Serine Protease Inhibitors

The serine protease plasmin, which is a normal blood constituent, has been shown to activate endogenous immunosuppressive mechanisms in osteoblast cells of animals. In addition, certain viruses incorporate plasmin into a maturation step of their life cycle. For example, influenza viruses require plasmin to cleave a viral coat protein in order for the viral particle to become infectious.

Active plasmin is derived from an inactive precursor, plasminogen, which must bind through a lysine binding site to a cell or tissue before it can be transformed into plasmin. Synthetic antifibrinolytic compounds have been shown to act as serine protease inhibitors by preventing the binding of plasminogen to tissue through a lysine binding site, thereby inhibiting the activation of plasmin from plasminogen. These serine protease inhibitors include epsilon-aminocaproic acid (EACA), trans-4-(aminomethyl) cyclohexanecarboxylic acid, and 4-aminomethylbenzoic acid, as well as derivatives thereof. Because they mimic the amino acid lysine in this mechanism of action, these compounds are often called lysine analogs.

The protective effect of protease inhibitors in virus-infected animals has been previously documented. For example, it has been found that an injection of protease inhibitors into mice and chickens, which were infected with lethal doses of influenza virus, prevented dissemination of the virus in the host organism. Zhirnov et al., Protective Effect of Protease Inhibitors in Influenza Virus Infected Animals, Archives of Virology 73, 263–272 (1982). In this study, it was shown that an injection of the lysine analog EACA, at the time of infection, greatly reduced the severity and duration of the viral infection.

Also, lysine analogs have been shown to exert an effect on the immune system of various organisms via a mechanism of action that is not completely understood. It has been shown that mice injected with a lysine analog and infected with influenza virus showed enhanced resistance to subsequent influenza virus reinfection without additional lysine analog injections. Lozitsky et al., Resistance of Mice to Reinfection After E-Aminocaproic Acid Treatment of Primary Influenza Virus Infection, Acta virol. 32, 117–122, 1988. This study concluded that EACA can stimulate the mechanisms of specific and non-specific antiviral protection of an organism.

Further, EACA has been parenterally administered in combination with an inactive influenza vaccine to enhance the protective action of the vaccine against influenza in mice. Lozitskii et al, Effectiveness of the Combined Use of an Inactivated Vaccine and a Proteolysis Inhibitor in the Prevention Of Experimental Influenza, Zh Mikrobiol Epidemiol Immunobiol (USSR) December 1985 (12) p. 49–53.

Other applications of serine protease inhibitors in the prevention and treatment of disease are revealed in additional scientific journal articles. In rats and mice, injections of lysine analogs reversed the immunosuppression associated with experimental acute pancreatitis and enhanced the survival of animals infected with staphylococci. (Chalyi, et al., Protease Inhibitors as Immunomodulators in Experimental Acute Pancreatitis and Staphylococcal Infection, Zh Mikrobiol Epidemiol Immunobiol (Russia), January–February 1993, p. 62–65.) Also, hamster lymphoid cells treated with a lysine analog (EACA) showed enhanced proliferation in culture. (Hart, et al., Effect of Protease Inhibitors On Mitogen Stimulation of Hamster Lymphoid Cells, Experimental Cell Research, 102(2):253–63, 1976 Oct. 15.) Further, the anticarcinogenic properties of orally administered EACA have been studied in rats. (Bespalov, et al., The Inhibiting Effect of Epsilon-Aminocaproic Acid on the Incidence of Induced Tumors of the Esophagus, Nervous System and Kidneys, Vopr Onkol (Russia), 1992 38(1), p. 69–74.

In addition to the scientific journal articles set forth above, the following United States patents disclose applications of lysine analogs in treatment methods:

U.S. Pat. No. 4,600,582 to Stevens et al. teaches that incorporation of certain lysine analogs into parenteral injections containing allergens reduces adverse allergic reactions caused by the allergens. The lysine analogs that Stevens discloses as being suitable include EACA and transexamic acid as well as derivatives of these compounds.

U.S. Pat. No. 3,692,904 to Tsutsumi teaches the use of lysine analogs to alleviate scours, which is a form of dysentery, in mammalian livestock. The lysine analogs employed in Tsutsumi's method include EACA, trans-4-(aminomethyl)cyclohexanecarboxylic acid, and 4-aminomethylbenzoic acid, as well as pharmaceutically acceptable salts of these compounds. This patent discloses that these lysine analogs can be administered intravenously by injection or orally by themselves or admixed with animal feed. Additionally, Tsutsumi states that these compounds can be used in combination with other medicaments commonly used for treatment of scours, including sulfa-drugs or antibiotics. While Tsutsumi's disclosure is directed primarily to the treatment of scours, this patent also teaches that the compounds may be used to prevent or reduce the frequency of scours when added to the animal feed on a regular basis.

The patent to Tsutsumi, however, does not specify the mechanism by which the lysine analogs treat or prevent scours. Likewise, Tsutsumi is silent as to any use for lysine analogues beyond treating a single specific disorder, scours, in domestic animals. Moreover, Tsutsumi does not teach or suggest administering lysine analogs to any animals other than mammals such as pigs (piglets), cows, sheep, horses (foals), and goats.

Parasitic Diseases

Parasitic diseases have plagued man and animals for millennia. Even today, it is estimated that parasitic diseases threaten over one quarter of the world's population. Two examples of parasites that infect higher organisms are helminths and protozoans. Parasitic helminths (worms) include certain species of Cestodes, which can cause cestodiasis; certain species of Digeneans, which can cause schistosomiasis; and certain species of Nematodes, which can cause filariasis.

The most serious parasitic diseases, however, are caused by protozoal infections. Protozoa are single-celled organisms that share characteristics of prokaryotic and eukaryotic organisms. Once classified taxonomically as a phylum within the kingdom Animalia, the term Protozoa is now applied to the animal-like members of the kingdom Protista. Many protozoa are harmless; however, others are parasites that cause serious diseases in many host organisms, including humans and their domestic livestock. The following are examples of several genera of protozoa and the diseases they cause:

| Genera | Disease |
| --- | --- |
| Cryptosporidium | cryptosporidiosis and spiking mortality |
| Eimeria | coccidiosis |
| Histomonas | blackhead |
| Leucocytozoon | leucocytozoonosis |
| Plasmodium | malaria |
| Toxoplasma | toxoplasmosis |
| Trichomonas | canker |
| Leishmania | leishmaniasis |
| Trypanosoma | sleeping sickness |
| Giardia | giardiasis |
| Babesia | babesiosis |
| Theileria | theileriosis |

In domestic poultry, coccidiosis is the most common protozoal disease. It is caused by several different species of protozoa known as coccidia, most of which are in the Eimeria genera. Coccidiosis is the most frequent cause of death in growing birds, usually striking chicks at three to six weeks of age. Coccidiosis afflicts the digestive tract of chickens, slowing growth rates and resulting in smaller, less marketable chickens if it does not kill them. Coccidiosis rarely causes overt symptoms, but is usually subclinical, evidenced only by losses in feed efficiency.

Eimeria protozoa infect nearly every kind of livestock, but each species of Eimeria is highly species specific; i.e., the coccidia that infect poultry do not affect other kinds of livestock, and vice versa. In poultry, coccidiosis is caused by several species of Eimeria protozoa. Different species generally prefer different portions of the birds' intestinal tracts, and one bird may be infected with more than one species at a time. $E.$ $acervulina$ is the most common cause of coccidiosis in North America. $E.$ $tenella$ and $E.$ $necatrix$ are the most serious, coming on rapidly and resulting in high death rates. Other species of Eimeria that cause coccidiosis include $E.$ $brunette,$ $E.$ $hagani,$ $E.$ $maxima,$ $E.$ $mitis,$ $E.$ $mivati,$ and $E.$ $proecox.$ Gradual exposure to coccidia or surviving an infection allows an individual bird to become immune to a particular species of coccidia. Immune birds typically do not become reinfected. To prevent and treat coccidiosis in poultry flocks, generally three methods are used: good management of the flock, including providing a clean environment and proper nutrition; the use of anticoccidial drugs; and vaccinations.

Anticoccidial drugs currently used to treat coccidia include Salinomycin, Amprolium, Sulfadimethoxine, Sulfamethazine, and Sulfaquinoxaline. While anticoccidials are often effective, the type of drug used and the dosage needed vary with the species of coccidia involved. Therefore, a battery of several different drugs is often required to treat a poultry flock infected with more than one type of coccidia. Some anticoccidials must be withdrawn from the birds a certain number of days before slaughter. Other problems with the use of anticoccidials are the same as with all antibiotics. For example, the target pathogens often develop a resistance to a particular drug. Additionally, antibiotics sometimes cause deleterious side effects, such as toxicity, vitamin deficiency, and, with chickens, damage to eggs. Additionally, anticoccidials are typically expensive to use, especially when more than one is required.

Vaccination against coccidia has met with some success in certain situations. A typical coccidial vaccine consists of a small amount of the actual protozoan that causes coccidiosis and is given to an animal in a dose large enough to trigger the natural immune response to the invading organism, yet small enough not to lead to extensive coccidial infestation of the animal. However, vaccination is seldom used for broiler chickens, because the mild infection produced by the vaccine slows the growth of the birds, making vaccination uneconomical. It is envisioned that genetically engineered antigens may one day be used to immunize young chicks.

Therefore, a need exists for an inexpensive method for combating parasitic diseases such as coccidiosis that does not result in organism resistance and does not cause the side effects typical of antibiotics, while at the same time addressing the problems inherent with vaccinations by either reducing the dose of the vaccine needed to prevent infection or by eliminating the need to vaccinate poultry against coccidia altogether.

OBJECTS AND SUMMARY OF THE INVENTION

In view of the above, an object of the present invention is to provide a method for combating parasitic diseases in animals and humans by the administration of serine protease inhibitors.

Another object of the present invention is to prevent parasitic diseases by prophylactically administering a serine protease inhibitor as an adjuvant in conjunction with a vaccine that is effective against the target parasite.

Another object of the present invention is to provide an oral adjuvant for administration in conjunction with a vaccine to enhance the immune response system and natural resistance of a host organism to a variety of infectious diseases.

Another object of the present invention is to enhance the immune response system and natural resistance of poultry to various infectious diseases by administering serine protease inhibitors to the avian species as an in ovo adjuvant in conjunction with a vaccine effective against the infectious disease.

It is a particular object of the present invention to prevent and treat coccidiosis in poultry by administering a serine protease inhibitor such as EACA to the poultry either by itself or as an adjuvant with an anti-coccidial vaccine.

The present invention meets these and other objectives by providing a method for combating a parasitic disease in an animal, which includes administering to the animal at least one lysine analog selected from the group consisting of epsilon-aminocaproic acid, trans-4-(aminomethyl) cyclohexanecarboxylic acid, 4-aminomethylbenzoic acid, and pharmaceutically acceptable derivatives thereof. Preferably, the lysine analog is continuously orally administered to the animal through the animal's diet, although the lysine analog may also be parenterally administered to the animal. The method of the present invention may be utilized to combat parasitic diseases caused at least in part by protozoa and/or a helminth.

Another aspect of the present invention is directed to a method for preventing a parasitic disease in any host organism by vaccinating the host organism against the parasitic disease and administering a lysine analog as a vaccine adjuvant to the host organism. For example, the parasitic disease may be caused by a protozoan, such as coccidia.

Yet another aspect of the present invention is directed to a method for orally administering to any host organism a lysine analog as an oral adjuvant to prevent an infectious disease in the host organism. The method includes vaccinating the host organism against the infectious disease and then continuously orally administering the lysine analog to the host organism after vaccinating the host organism.

Still another aspect of the present invention is directed to preventing an infectious disease in poultry by vaccinating the poultry against the infectious disease in ovo and administering a lysine analog in ovo to the poultry as a vaccine adjuvant. Preferably, after hatching, the diet of the poultry is supplemented with the lysine analog in an amount of at least approximately 10 ppm and continuously fed to the poultry.

A particular aspect of the present invention is directed to a method for enhancing the immune response and natural resistance of poultry against coccidia by supplementing a diet of the poultry with a lysine analog selected from the group consisting of epsilon-aminocaproic acid, trans-4-(aminomethyl)cyclohexanecarboxylic acid, 4-aminomethylbenzoic acid, and pharmaceutically acceptable derivatives thereof, in an amount of at least approximately 10 ppm, and continuously feeding the supplemented diet to the poultry from hatching. The lysine analog may also be used as a vaccine adjuvant in conjunction with an anti-coccidial vaccine.

Other aspects and advantages of the present invention will become apparent and obvious from a study of the following description.

DETAILED DESCRIPTION OF THE INVENTION

The present invention is a method for combating infectious diseases in humans and animals by the administration of a lysine analog. The lysine analog used may be any serine protease inhibitor that acts to inhibit the activation of plasminogen to plasmin. Examples of serine protease inhibitors that are contemplated as being utilized to carry out all embodiments of the present invention are the same lysine analogs and derivatives thereof that are described in U.S. Pat. No. 4,600,582 to Stevens, which is hereby expressly incorporated by reference. In the preferred method of the present invention, epsilon-aminocaproic acid (EACA) is used, and for brevity this will be the lysine analog referred to hereafter. It is contemplated that any conventional route of administration may be employed, including oral administration, in ovo administration, and/or parenteral administration.

It is contemplated that the present invention can be employed to combat a variety of disease, such as parasitic infections, in any host organism by way of enhancing the immune system of the host organism. As used herein, the term "parasite" refers to parasitic organisms classified in either the kingdom Protista or the kingdom Animalia. For example, the inventive method can be employed to combat parasitic diseases caused at least in part by any of the helminths and/or protozoans listed above in the "Background of the Invention." However, in the preferred embodiment, the present invention is particularly directed to preventing and treating coccidial infections in avian species, such as domestic chickens or other poultry. In the preferred method of administration, the birds' daily dietary intake of feed or water is supplemented with EACA in an amount of approximately 10 parts-per-million (ppm) to 2000 ppm. Accordingly, the each bird will receive 1 to 200 mg/kg of body weight/day. Through continuous oral administration through the birds' diet, EACA enhances the birds' natural immune response to coccidial organisms and enables the birds to combat these and other pathogens without the need to administer antibiotics or other anti-coccidial drugs.

The method of the present invention is designed to be used throughout the entire life cycle to provide continuous protection against coccidia. Alternately, EACA can be administered to young chicks only until protective immunity is established or until withdrawal a certain time before slaughter is required by law. EACA may be dietarily administered, as set out above, or may be administered in ovo before the chicks hatch. Additionally, the method of the present invention can be employed on a remedial basis to treat infected birds that demonstrate symptoms of coccidia at any stage in life. Although the method of the present invention is primarily directed to preventing and treating coccidia in poultry, the method of the present invention can also be employed to prevent and/or treat other parasitic diseases in animals and humans as well, such as cryptosporidiosis, blackhead, leucocytozoonosis, leishmaniasis, malaria, toxoplasmosis, canker, sleeping sickness, giardiasis, babesiosis, theileriosis, cestodiasis, schistosomiasis, and filariasis.

In another aspect of the present invention, it is postulated that infectious diseases may be prevented in humans and animals by prophylactically administering a lysine analog as an oral or in ovo adjuvant in conjunction with a vaccine or other species-specific treatment. As described earlier, the lysine analog used may be any serine protease inhibitor that acts to inhibit the activation of plasminogen to plasmin, such as EACA. The administering of EACA as an oral or in ovo adjuvant may be used to prevent and/or treat a variety of diseases, including but not limited to the following: salmonellosis; colibacillosis; tuberculosis; infectious coryza; mycoplasmosis; campylobacteriosis; erysipelas; clostridial diseases; bordetellosis (turkey coryza); staphylococcosis; streptococcosis; spirochetosis; chlamydiosis (ornithosis); Marek's disease; infectious bronchitis; laryngotracheitis; Newcastle disease and other paramyxovirus infections; avian encephalomyelitis; influenza; adenovirus infections; pox; duck virus hepatitis; duck virus enteritis (duck plague); coronaviral enteritis of turkeys (bluecomb disease); spiking mortality of turkeys; rotavirus infections; astrovirus infections; reovirus infections; and infectious bursal disease.

It is particularly contemplated that use of a lysine analog can be employed as an adjuvant to combat a variety of parasitic diseases in any host organism by enhancing the immune system of the host organism. However, in the preferred embodiment, the method of using a lysine analog as an adjuvant is particularly directed to preventing and treating protozoal infections in avian species, such as coccidia in domestic chickens or other poultry, by administering the lysine analog in conjunction with an anti-coccidial vaccine. Preferably administered to the birds orally as part of their daily dietary intake of feed or water, EACA as an adjuvant permits less of the vaccine to be used to produce a given degree of protection than without the EACA. By using less of the vaccine, there is a lower chance that significant coccidial infection will result from the vaccine itself. If the poultry are vaccinated in ovo before hatching, EACA may be also be administered in ovo along with the vaccine as an adjuvant. EACA, whether administered in ovo or dietarily or both, enhances the birds' natural immune response to coccidial organisms and enables the birds to combat the parasites more effectively than they could through the administration of the vaccine alone.

Having now generally described the invention, a further understanding can be obtained by reference to the following specific examples, which are provided herein for purposes of illustration only and are not intended to be limiting in any manner.

EXAMPLE 1

To test whether a lysine analog fed in the diet could enhance the immune response of birds and whether the compound was effective against protozoa, chickens were fed EACA and then exposed to the protozoal parasite Eimeria tenella, a cause of coccidiosis. The magnitude of the cecal lesions, which is an indicator of the severity of infection, was evaluated in each bird to determine if EACA conferred any benefit to the animals.

Materials And Methods

Newly-hatched chicks were immediately placed on diets containing 200 ppm EACA, 1000 ppm EACA, no medication, or 65.5 ppm Salinomycin Sodium (Bio-Cox), a highly effective FDA-approved anti-coccidial routinely used in the poultry industry. Bio-Cox is the trade name for Salinomycin, 0.004–0.0066%, which is distributed by American Home Products and Pfizer. At three weeks of age, the birds were individually gavaged with 50,000 oocysts of Eimeria tenella, a coccidia that preferentially infects the cecum. The birds were monitored, and when the unmedicated controls showed overt signs of coccidiosis, the birds were sacrificed and the ceca were scored for the severity of lesions by a qualified investigator.

Results

The unmedicated, unchallenged group of birds (negative control) served as an example of a normal cecum. These ceca gave low lesion scores (Table 1). The unmedicated, challenged birds (positive control) were examples of diseased ceca, which gave a score of 3.05. The Bio-Cox-medicated birds showed protection against the coccidial infection, as evidenced by a score of 1.28. The 200 ppm EACA-medicated birds showed no protection. The 1000 ppm EACA-medicated birds showed protection against the coccidial infection, with a lesion score of 1.85. Thus, the Biocox-treated birds and the 1000 ppm EACA-treated birds had lesions which were significantly less severe (p<0.05) than the unmedicated positive control group.

TABLE 1

Lesion Scores

| Treatment | Lesion Score |
| --- | --- |
| Unmedicated feed, unchallenged | 0.15 |
| Unmedicated feed, challenged | 3.05 |
| Bio-Cox, challenged | 1.28 |
| EACA, 200 ppm, challenged | 2.95 |
| EACA, 1000 ppm, challenged | 1.85 |

The feed consumption data (Table 2) shows that between three and four weeks of age, the birds were receiving approximately 4.25 mg EACA/kg body weight/hour on the 1000 ppm EACA diet.

TABLE 2

Feed Consumption Data

| Treatment | 3 wk pen wt (g) | 4 wk pen wt (g) | Feed consumption (g) | mg EACA/ kg avg body wt/day |
| --- | --- | --- | --- | --- |
| Unmedicated feed, unchallenged | 6700 | 10580 | 6614 | |
| Unmedicated feed, challenged | 6830 | 10640 | 6705 | |
| Bio-Cox, challenged | 7410 | 11410 | 6842 | |
| EACA, 200 ppm, challenged | 6640 | 9870 | 5846 | 20.23 |
| EACA, 1000 ppm, challenged | 6830 | 10170 | 6067 | 102 |

EXAMPLE 2

To demonstrate the effectiveness of a lysine analog administered as an adjuvant to prevent parasitic infections such as coccidia, the following method is performed:

Newly-hatched chicks are divided into the following three treatment groups:

Group 1—(Negative Control) This group receives no vaccine nor any EACA.

Group 2—(Positive Control) This group receives Coccivax (Sterwin), which is a coccidial vaccine, in the eye on day 1 and no EACA.

Group 3—(Test Group) This group receives Coccivax in the eye on day 1 and 1000 ppm EACA in the feed for thirteen days.

All groups are housed in floorpens with feed and water supplied ad libitum. The houses are on 24-hour light.

At 10 days of age, group 3 are switched to a diet without EACA.

At 13–15 days of age, birds from each group are gavaged with 10,000, 20,000, 50,000, or 100,000 oocysts of E. tenella. A range of gavage doses are used because of variability of the virulence of the oocysts.

The ceca are lesion scored at approximately 7 days after the gavaging, based on the appearance of overt clinical signs in the negative control (Group 1).

It is postulated that Group 3 will enjoy enhanced resistance to coccidial infection even when administered a lower-than-normal quantity of anti-coccidial vaccine. The administration of EACA as an adjuvant enhances the natural immune response to the vaccine. It is postulated that the deleterious effects of anti-coccidial vaccines can be markedly reduced or even eliminated by administering EACA as an adjuvant along with a reduced quantity of vaccine. Alternately, more protection can be obtained by using a standard dose of vaccine in conjunction with EACA.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method for combating coccidiosis in an animal of avian species, comprising the step of administering at least one lysine analog to the animal in ovo, wherein said analog is selected from the group consisting of epsilon-aminocaproic acid (EACA), trans-4-(aminomethyl) cyclohexanecarboxylic acid, and 4-aminomethylbenzoic acid.

2. The method of claim 1 wherein the lysine analog is further administered with a coccidial vaccine.

* * * * *